United States Patent [19]

Reedy et al.

[11] 4,059,607
[45] Nov. 22, 1977

[54] PREPARATION OF HYDROCARBON CHLOROSILANES FROM POLYSILANES

[75] Inventors: James Dale Reedy, New Fairfield, Conn.; Thomas Harold Barker, Newport, Ohio

[73] Assignee: Union Carbide Corporation, New York, N.Y.

[21] Appl. No.: 752,811

[22] Filed: Dec. 20, 1976

[51] Int. Cl.$^2$ .............................................. C07F 7/12
[52] U.S. Cl. ............................................. 260/448.2 E
[58] Field of Search ................................. 260/448.2 E

[56] References Cited

U.S. PATENT DOCUMENTS

| | | | |
|---|---|---|---|
| 2,474,087 | 6/1949 | Barry et al. | 260/448.2 E |
| 3,878,234 | 4/1975 | Atwell et al. | 260/448.2 E |

OTHER PUBLICATIONS

"Journal of Organometallic Chemistry", 96, C-1-C3, 1975.

Primary Examiner—Paul F. Shaver
Attorney, Agent, or Firm—Eugene C. Trautlein

[57] ABSTRACT

The present invention relates to a method for producing high yields of hydrocarbon chlorosilanes by reacting polysilanes with alkyl or alkenyl chloride at a temperature ranging from about 10° C to about 60° C in the presence of a co-catalyst system. The co-catalyst system is comprised of a combined catalytic amount of co-catalyst (a) and co-catalyst (b), wherein co-catalyst (a) is selected from the group consisting of $R'_3N$, $R'_3NHCl$, $R'_4NCl$ and $R'_4PCl$ wherein $R'$ is one or more of an alkyl or aralkyl radical of from 1 to 18 carbon atoms and co-catalyst (b) is selected from the group consisting of metal salts and metal complexes.

14 Claims, No Drawings

PREPARATION OF HYDROCARBON CHLOROSILANES FROM POLYSILANES

BACKGROUND AND DESCRIPTION OF THE PRIOR ART

This invention relates to a novel process for the preparation of hydrocarbon chlorosilanes. That is, the present invention relates to a process for producing high yields of alkyl, alkenyl or aralkyl chlorosilanes by reacting polysilanes (i.e., silicon compounds which contain one or more Si—Si units) with alkyl or alkenyl chloride at a temperature ranging from about 10° C to about 60° C in the presence of amine (or phosphine) and metal salt (or complex) co-catalysts.

U.S. Pat. No. 3,878,234 discloses the preparation of hydrocarbon silanes by reacting methylchloropolysilanes or chloropolysilanes with hydrocarbon chlorides in the presence of a tertiary amine, the chloride salt of a tertiary amine, or a hydrocarbon phosphonium chloride catalyst at a temperature of from 30° to 250° C. However, the yields of hydrocarbon silane disclosed in the examples of that patent varied widely from 0% to 87% depending upon the temperature (75° to 125° C) and catalyst used. The reaction times given in that patent range from 12 to 200 hours.

A recent publication (Journal of Organometallic Chemistry 85, CL (1975)) discloses that halobenzenes can be reacted with disilanes to give arylsilanes in the presence of a palladium complex catalyst. The publication discloses temperatures ranging from 120° C to 170° C and reaction times between 18 and 33 hours. Also, the publication does not disclose reactions using alkyl halides as a reactant.

Another recent publication (Journal of Organometallic Chemistry 96, C1-C3 (1975)) discloses the reaction of allylchloride with trichlorosilane using a stoichiometric amount of a tertiary amine in the presence of a metallic salt catalyst. Such a reaction involves the cleavage of the hydrogen-silicon bond of the trichlorosilane to form allyl trichlorosilane and amine hydrochloride. The amine hydrochloride is regarded to be an undesirable byproduct of the reaction.

U.S. Pat. No. 2,474,087 discloses the reaction of hydrocarbon halides with hexachlorodisilane to produce hydrocarbon halosilanes either without a catalyst or with a cuprous chloride, antimony trichloride, or mercuric chloride catalyst. All examples in that patent disclose reaction temperatures ranging from 200° to 350° C.

U.S. Pat. No. 2,709,176 discloses the reaction of polysilanes with hydrogen chloride in the presence of tertiary amines or their halide salts to produce silanes having a higher SiH content than that contained in the reactants. This reaction does not establish any new silicon-carbon bonds but merely establishes silicon-hydrogen and silicon-chlorine bonds.

U.S. Pat. Nos. 2,598,435 and 2,842,580 disclose the rearrangement of methyl and chlorine substituted silanes to produce monosilane and polysilanes. In this reaction no new carbon-silicon bonds are formed except by rearrangement.

SUMMARY OF THE INVENTION

The present invention relates in part to a process of reacting alkyl or alkenyl chlorides with polysilanes to produce high yields of hydrocarbon chlorosilanes at low temperatures (i.e., from about 10° C to about 60° C) with short reaction times of, for example, less than about 10 hours.

The process for production of organochlorosilanes that is disclosed in this invention is characterized by a co-catalyst system comprised of a combined catalytic amount of co-catalyst (a) and co-catalyst (b), wherein co-catalyst (a) is one or more of $R'_3N$, $R'_3NHCl$, $R'_4NCl$ and $R'_4PCl$ in which R' is one or more of an alkyl or aralkyl radical of from 1 to 18 carbon atoms, and co-catalyst (b) is selected from the group consisting of metal salts and metal complexes.

DESCRIPTION OF THE PREFERRED EMBODIMENTS

This invention relates to a process of reacting $$RCl \qquad (1)$$

with a polysilane consisting of units of the formula:

$$Me_xCl_ySi \qquad (2)$$

to produce $RMe_xSiCl_{3-x}$, which comprises carrying out the reaction in contact with a combined catalytic amount of co-catalyst (a) and co-catalyst (b). Co-catalyst (a) is selected from the group consisting of $R'_3N$, $R'_3NHCl$, $R'_4NCl$ and $R'_4PCl$, and co-catalyst (b) is selected from the group consisting of metal salts and metal complexes. The reaction is effected at a temperature from about 10° C to about 60° C. In the above formulas, R is an alkyl radical of from 1 to 18 carbon atoms, an alkenyl radical of from 2 to 18 carbon atoms, or an aralkyl radical of from 7 to 18 carbon atoms, $x$ is 0 to 2, $y$ is 0 to 3, the sum of $x$ and $y$ being from 2 to 3 with the proviso that at least one silicon atom of the polysilane be bonded to at least one chlorine group; all the silicon atoms in (2) being bonded to at least one other silicon atom and all the valences of the silicon atoms in (2) being satisfied by other silicon atoms, Cl or Me radicals, and R' is one or more of an alkyl or aralkyl radical of from 1 to 18 carbon atoms.

The process of this invention is carried out by reacting (1) and (2) in the presence of the catalysts at a temperature of from about 10° to about 60° C. Although a wide range of temperatures may be used according to the method of the instant invention, ranging from 0° C to 200° C, there is no advantage to the use of high or low temperatures. Therefore, a temperature of from about 10° C to about 60° C is preferred for the process of the invention. Room temperature is the most preferred temperature for the process of the invention. Although super- or sub-atmospheric pressure may be used in the process of the invention, atmospheric pressure is preferred unless low boiling solvents are used. Reaction time is generally less than 10 hours, but it may be longer if desired for some purpose.

The process of the invention can be carried out in the presence or absence of a solvent. The amount of solvent employed, if used, is not critical and the primary purpose of the solvent is to facilitate handling of the reaction mixture. If employed, the solvents are those which do not react with chlorosilanes (i.e., inert to the reaction) and can be any such solvent such as hydrocarbons, such as benzene, tolylene, pentane, and the like; or any halohydrocarbon such as chlorobenzene, or chlorotolylene; ethers such as dibutyl ether, or the dimethyl ether of ethylene glycol; or nitriles such as acetonitrile.

The polysilanes which are useful in the process of the present invention are well-known in the art. For example, hexachlorodisilane and octachlorotrisilane are byproducts in the commercial preparation of trichlorosilane from silicon metal and hydrogen chloride. Polysilane byproducts of the reaction of methyl chloride with silicon metal include $Cl_2CH_3SiSiCH_3Cl_2$, $Cl_2CH_3SiSi(CH_3)_2Cl$, and $Cl(CH_3)_2SiSi(CH_3)_2Cl$. Specific examples of useful polysilanes include: hexachlorodisilane, 1,1-dimethyltetrachlorodisilane, 1,2-dimethyltetrachlorodisilane, and 1,1,2,2-tetramethyldichlorodisilane. Also useful are polymeric silanes having more than two silicon atoms such as octachlorotrisilane and dodecylchloropentasilane.

As is indicated above, the nucleophile (i.e. co-catalyst (a) above) useful in the process of the invention is selected from the group consisting of tertiary amines, chloride salts of tertiary amines, quarternary ammonium chlorides and quarternary phosphonium chlorides. In the formulas for co-catalyst (a) given about R' is one or more of any alkyl radical of from 1 to 18 carbon atoms, such as methyl, ethyl, butyl, propyl, isopropyl, t-butyl, octyl, dodecyl, or octadecyl, and any aralkyl radical of from 7 to 18 carbon atoms such as benzyl, beta-phenylpropyl, beta-phenylethyl, tolylmethyl, xenylethyl, beta-naphthylethyl, or omega-phenylhexyl.

The metal salts and metal complexes useful as co-catalyst (b) in the invention typically contain a cation selected from the group consisting of metals with atomic numbers 22 to 30, 40 to 48, 58 to 80 and 90 to 92 inclusive. The preferred cations include Ni(II), Cu(I) and Cu(II). The counter ions useful in the metal salts include halide, oxide, sulfide, sulfate, nitrate, chlorate, perchlorate, hexafluorophosphate, acetylacetonate, carboxylate and oxylate. The preferred anions are chloride and acetylacetonate. Neutral chelating groups useful in the metal complexes include carbon monoxide, mercaptan, trifluorophosphene, ether, aryl, alkene and alkyne. Examples of useful co-catalysts include $ZnCl_2$, $FeCl_2$, $CoCl_2$, $CuCl$, $AgPF_6$ and nickel acetylacetonate.

The combined amount of the co-catalysts employed in the process of this invention is not narrowly critical as long as a catalytic amount is present. The combined amount of co-catalysts (a) and (b) can vary between about 0.01 and about 10 percent based on the total weight of reactants (1) and (2).

The process of the present invention involves a reaction in which cleavage of the silicon-silicon bond in the above-mentioned polysilanes takes place to form a silicon-carbon bond and a silicon-chlorine bond to produce silicon tetrachloride and $RMe_xSiCl_{3-x}$ wherein R and x are defined above.

The following examples are given by way of illustration only in order to describe the invention in greater detail, and are not intended to limit the scope thereof.

As used herein, "Me" denotes the methyl group and "%" denotes weight percent.

EXAMPLES

EXAMPLE I

To a 100 ml three neck round bottom flask equipped with a thermometer, magnetic stirrer and rubber septum was added 0.25 grams (0.0025 mole) of cuprous chloride, 65 grams of o-dichlorobenzene and 0.25 grams (0.0014 mole) of tributylamine in a nitrogen atmosphere. A mixture of 5.2. grams $Si_2Cl_6$ (0.019 mole) and 1.6 grams (0.021 mole) of allyl chloride was added to the stirred flask in 1 cubic centimeter increments over a period of 6 minutes. During this time the temperature increased from 25° C to 29° C. A sample was taken from the flask 30 minutes after the final addition. It was analyzed 2 hours later by vapor-phase chromatography and found to contain 4.2 wt. % allyltrichlorosilane (91.3% yield), 4.2 wt. % $SiCl_4$, 0 wt. % $Si_2Cl_6$, a trace of allyl chloride and 91.1 wt. % o-dichlorobenzene.

EXAMPLE II

Repeating Example I except that the cuprous chloride co-catalyst was omitted, a sample was taken 1 hour after the addition of reactants and analyzed 1 hour later by vapor-phase chromatography. It was found to contain 0.1% allyltrichlorosilane (4.4% yield), 3.6% $SiCl_4$, 3.0% allyl chloride, a trace of $Si_2Cl_6$ and 92% o-dichlorobenzene. Thus, the predominant reaction was the disproportionation of $Si_2Cl_6$ to $SiCl_4$ and higher molecular weight polysilanes, a well known reaction. Another sample was taken 26 hours after the final addition of reactants and analyzed 24 hours later. It contained 0.2 wt. % allyltrichlorosilane, 2.5% allyl chloride, 4.5 wt. % $SiCl_4$ and a trace of $Si_2Cl_6$.

EXAMPLE III

Repeating Example I except that the tributylamine co-catalyst was omitted, no reaction was observed 21 hours after the addition of reactants. After that time, a sample was analyzed by vapor-phase chromatography and found to contain less than 1 wt. % allyltrichlorosilane (<22% yield), 2.5 wt. % allyl chloride, 4.1 wt. % $Si_2Cl_6$, 0.5 wt. % $SiCl_4$ and 92.6 wt. % o-dichlorobenzene. Thus, the metal salt (cuprous chloride) has not been found effective as a sole catalyst under the reaction conditions of this example.

EXAMPLES IV to X

These examples utilize the same reactants and procedure used in Example I. Various solvents, and metal salt and amine co-catalysts are used as presented in Table I.

The results are given in Table I which follows.

TABLE I

| Example No. | Reaction Charge Solvent Name | Wt % | Amine Co-Catalyst Name | Wt % | Metal Salt Co-Catalyst Name[7] | Wt % | Allyl Chloride Wt % | $Si_2Cl_6$ Wt % | Time To Sample[1] Hours | Time To Analysis[2] Hours | Product Analysis[10] Solvent Wt % | Allyl Chloride Wt % | $Cl_3Si$-$CH_2CH$=$CH_2$ Wt % | % Yield | $SiCl_4$ | $Si_2Cl_6$ |
|---|---|---|---|---|---|---|---|---|---|---|---|---|---|---|---|---|
| IV | Acetonitrile | 58.4 | TEA[4] | 1.0 | $Ni(AcAc)_2$ | 1.0 | 7.5 | 24.1 | 0.5 | 3.0 | 45.1 | /8/ | 12.6 | 80.3 | 26.1 | <0.1 |
|  |  |  |  |  |  |  |  |  | 3.0 | 5.0 | 47.9 | /8/ | 14.0 | 89.2 | 23.4 | <0.1 |
|  |  |  |  |  |  |  |  |  | 20.0 | 27.0 | 47.2 | /8/ | 13.5 | 86.0 | 20.1 | <0.1 |
| V | Acetonitrile | 64.3 | TEA[4] | 1.0 | $AgPF_6$ | 1.0 | 8.2 | 26.5 | 0.5 | 3.0 | 68.5 | /8/ | 5.6 | 32.6 | 21.3 | <0.1 |
|  |  |  |  |  |  |  |  |  | 2.0 | 3.5 | 71.1 | /8/ | 4.2 | 24.4 | 19.7 | <0.1 |
|  |  |  |  |  |  |  |  |  | 19.0 | 26.5 | 68.2 | /8/ | 6.5 | 37.8 | 14.8 | <0.1 |
| VI | Acetonitrile | 61.9 | TEA[4] | 4.7 | $ZnCl_2$ | 1.0 | 7.9 | 25.5 | 0.5 | 23.0 | 72.5 | /8/ | 6.9 | 41.6 | 14.8 | <0.1 |
|  |  |  |  |  |  |  |  |  | 2.0 | 23.5 | 71.6 | /8/ | 5.6 | 33.7 | 15.2 | <0.1 |
| VII | Acetonitrile | 61.9 | TEA[4] | 4.7 | $FeCl_2$ | 1.0 | 7.9 | 25.5 | 0.5 | 3.5 | 56.8 | /8/ | 16.9 | 100+ | 12.4 | ND[9] |
|  |  |  |  |  |  |  |  |  | 2.0 | 4.0 | 59.4 | /8/ | 15.7 | 94.6 | 14.0 | ND[9] |
| VIII | Acetonitrile | 61.9 | TEA[4] | 4.7 | $CoCl_2$ | 1.0 | 7.9 | 25.5 | 0.5 | 4.0 | 55.4 | /8/ | 17.6 | 100+ | 17.0 | ND[9] |
|  |  |  |  |  |  |  |  |  | 2.0 | 4.5 | 56.0 | /8/ | 16.5 | 99.4 | 17.0 | ND[9] |
| IX | o-DCB[3] | 77.0 | HMPA[5] | 0.2 | CuCl | 0.2 | 5.4 | 17.4 | 0.5 | 1.5 | 78.2 | 0.6 | 10.9 | 96.5 | 9.6 | ND[9] |
|  |  |  |  |  |  |  |  |  | 2.0 | 3.0 | 77.6 | 0.6 | 10.9 | 96.5 | 10.1 | ND[9] |
| X | o-DCB[3] | 77.0 | TPAC[6] | 0.2 | CuCl | 0.2 | 5.4 | 17.4 | 0.5 | 1.8 | 78.1 | 0.6 | 10.7 | 94.7 | 9.7 | ND[9] |
|  |  |  |  |  |  |  |  |  | 2.0 | 3.0 | 78.3 | 0.6 | 10.7 | 94.7 | 9.7 | ND[9] |

NOTES:
[1]Time elapsed from addition of reactants to sampling of product.
[2]Time elapsed from addition of reactants to analysis of product.
[3]o-Dichlorobenzene.
[4]Triethylamine.
[5]Hexamethylphosphoramide.
[6]Tetrapentylammonium chloride.
[7]Nickel acetylacetonate.
[8]The amount of allyl chloride is contained in the solvent wt % because of the difficulty in separating these two materials in the vapor-phase chromatography analysis.
[9]Non-detectable.
[10]All reactions carried out at about 25° to 29° C and atmospheric pressure.

As is shown in Table I, high yields of alkylated silane are achieved using the process of the invention at reaction temperatures of about 25° to 29° C and atmospheric pressure. Reaction times can be short and no economic advantage is obtained by extending the reaction time beyond a preferred minimum. As is indicated in Example IX, a yield of 96.5% of $Cl_3SiCH_2CH=CH_2$ is achieved when the time from addition of reactants to sampling is 0.5 hour and the time from addition of reactants to analysis of product is 1.5 hours. It is noted that the same percent yield is achieved (96.5% yield) in Example IX when the time to sample is 2.0 hours and the time to analysis is 3.0 hours.

What is claimed is:

1. A process of reacting $$RCl \qquad (1)$$

with a polysilane consisting of units of the formula:

$$Me_xCl_ySi \qquad (2)$$

to produce $RMe_xSiCl_{3-x}$, which comprises carrying out the reaction in contact with a combined catalytic amount of co-catalyst (a) and co-catalyst (b), wherein co-catalyst (a) is selected from the group consisting of $R'_3N$, $R'_3NHCl$, $R'_4NCl$ and $R'_4PCl$, and co-catalyst (b) is selected from the group consisting of metal salts and metal complexes, at a temperature of from about 10° C to about 60° C, wherein R is an alkyl radical of from 1 to 18 carbon atoms, an alkenyl radical of from 2 to 18 carbon atoms, or an aralkyl radical of from 7 to 18 carbon atoms, x is 0 to 2, y is 0 to 3, the sum of x and y being from 2 to 3 with the proviso that at least one silicon atom of the polysilane be bonded to at least one chlorine group; all the silicon atoms in (2) being bonded to at least one other silicon atom and all the valences of the silicon atoms in (2) being satisfied by other silicon atoms, Cl or Me radicals, and R' is one or more of an alkyl or aralkyl radical of from 1 to 18 carbon atoms.

2. The process of claim 1, wherein co-catalyst (a) is $R'_3N$ wherein R' is an alkyl or aralkyl radical of from 1 to 18 carbon atoms.

3. The process of claim 1 wherein co-catalyst (a) is tributylamine.

4. The process of claim 1 wherein co-catalyst (a) is triethylamine.

5. The process of claim 1 wherein co-catalyst (a) is hexamethylphosphoramide.

6. The process of claim 1 wherein co-catalyst (a) is tetrapentyl ammonium chloride.

7. The process of claim 1 wherein co-catalyst (b) is cuprous chloride.

8. The process of claim 1 wherein co-catalyst (b) is zinc chloride.

9. The process of claim 1 wherein co-catalyst (b) is cobalt chloride.

10. The process of claim 1 wherein co-catalyst (b) is $AgPF_6$.

11. The process of claim 1 wherein co-catalyst (b) is nickel acetylacetonate.

12. The process of claim 1 wherein (1) is allyl chloride.

13. The process of claim 1 wherein (1) is benzyl chloride.

14. The process of claim 1 wherein (1) is crotyl chloride.

* * * * *